(12) United States Patent
Kachanov et al.

(10) Patent No.: US 7,259,856 B2
(45) Date of Patent: Aug. 21, 2007

(54) METHOD FOR THE PRECISE MEASUREMENT OF THE WAVELENGTH OF LIGHT

(75) Inventors: Alexander Kachanov, Sunnyvale, CA (US); Sze Tan, Sunnyvale, CA (US); Barbara Paldus, Portola Valley, CA (US)

(73) Assignee: Picarro, Inc., Sunnyvale, CA (US)

( * ) Notice: Subject to any disclaimer, the term of this patent is extended or adjusted under 35 U.S.C. 154(b) by 244 days.

(21) Appl. No.: 11/059,198

(22) Filed: Feb. 16, 2005

(65) Prior Publication Data

US 2006/0181710 A1    Aug. 17, 2006

(51) Int. Cl.
*G01N 21/00* (2006.01)
(52) U.S. Cl. ..................................................... 356/437
(58) Field of Classification Search ................ 356/402, 356/484, 432, 300, 437–439; 436/164; 422/82.05, 422/82.09, 82.11; 702/23–24, 32, 140, 187–194, 702/199
See application file for complete search history.

(56) References Cited

U.S. PATENT DOCUMENTS

| | | | | |
|---|---|---|---|---|
| 5,528,040 A | * | 6/1996 | Lehmann | 250/343 |
| 6,795,190 B1 | * | 9/2004 | Paul et al. | 356/437 |
| 7,012,696 B2 | * | 3/2006 | Orr et al. | 356/454 |
| 7,050,170 B2 | * | 5/2006 | Chilese et al. | 356/437 |
| 2003/0189711 A1 | * | 10/2003 | Orr et al. | 356/484 |
| 2004/0065816 A1 | * | 4/2004 | Ye et al. | 250/227.18 |
| 2005/0012931 A1 | * | 1/2005 | Tan et al. | 356/437 |

* cited by examiner

*Primary Examiner*—Tarifur Chowdhury
*Assistant Examiner*—Jonathon D Cook
(74) *Attorney, Agent, or Firm*—Lumen Intellectual Property Services, Inc.

(57) ABSTRACT

Improved cavity ring down spectroscopy is provided by binning decay time vs. wavelength data into wavelength bins defined by discontinuities in a wavelength monitor signal. Average decay times and average wavelengths are computed for each bin. The optical loss of a target analyte at the average wavelengths is determined from the corresponding average decay times.

9 Claims, 16 Drawing Sheets

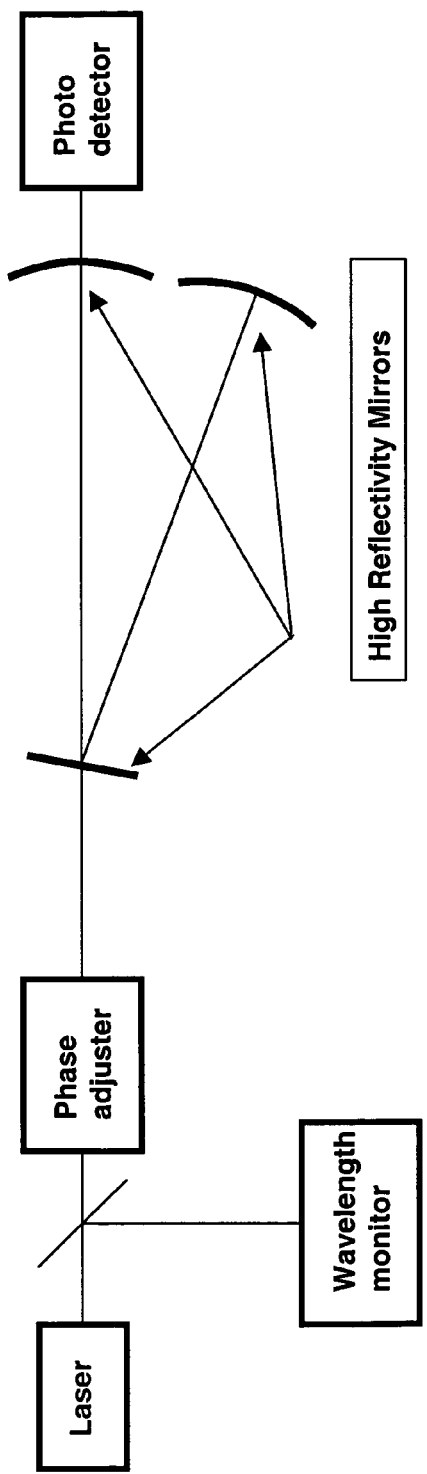
Fig. 15-a.

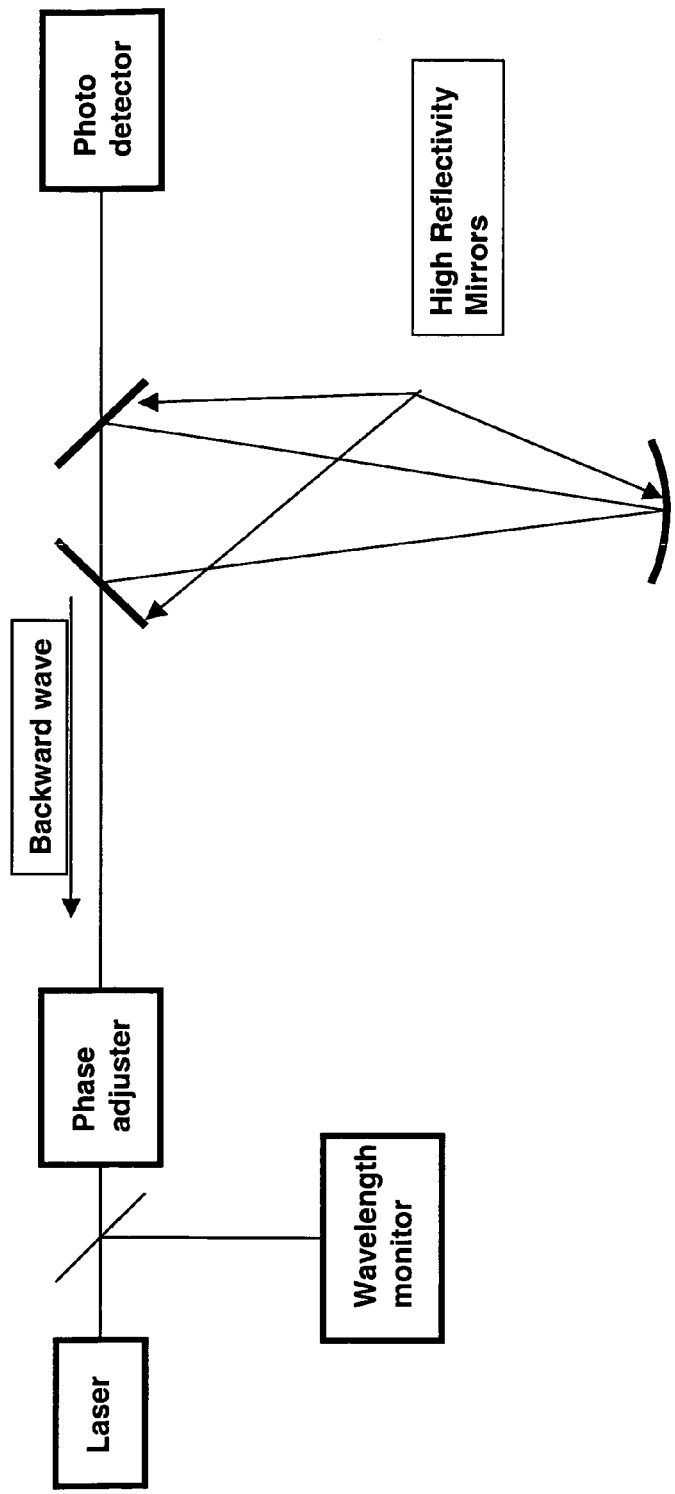
Fig. 15-b.

METHOD FOR THE PRECISE MEASUREMENT OF THE WAVELENGTH OF LIGHT

FIELD OF THE INVENTION

This invention relates to a method for using the free spectral range of an optical resonator in conjunction with a coarse wavelength monitor having an output that is a monotonic function of wavelength to precisely measure the wavelengths in a spectral scan. The precision of the wavelength measurement exceeds the precision of the coarse wavelength monitor. The cavity enhanced optical spectrometer can be either a cavity ringdown spectrometer (CRDS) or a cavity enhanced absorption spectrometer (CEAS).

BACKGROUND OF THE INVENTION

Molecular absorption spectroscopy is a technique that uses the interaction of energy with a molecular species to qualitatively and/or quantitatively study the species, and/or to study physical processes associated with the species. The interaction of radiation with matter can cause redirection of the radiation and/or transitions between the energy levels of the atoms or molecules. The transition from a lower level to a higher level with an accompanying transfer of energy from the radiation to the atom or molecule is called absorption. When molecules absorb light, the incoming energy excites a quantized structure to a higher energy level. The type of excitation depends on the wavelength of the light. Electrons are promoted to higher orbitals by ultraviolet or visible light, vibrations are excited by infrared light, and rotations are excited by microwaves. The infrared (IR) region is generally considered as extending from just beyond the red visible region (~0.7 μm to 50 μm). The 0.7 to 2.5 μm region is generally called the near-infrared (NIR), the 2.5 to 15 μm region is referred to as the mid-infrared and the 15 to 50 μm region is called the far-infrared. The wavelengths of IR absorption bands are characteristic of specific types of chemical bonds, and IR spectroscopy finds its greatest utility in the identification of organic and organometallic molecules.

The data that is obtained from spectroscopy is called a spectrum. An absorption spectrum shows the absorption of light as a function of its wavelength. The spectrum of an atom or molecule depends on its energy level structure. A spectrum can be used to obtain information about atomic and molecular energy levels, molecular geometries, chemical bonds, the interactions of molecules, and related processes. Often, spectra are used to identify the components of a sample (qualitative analysis). Spectra may also be used to measure the amount of material in a sample (quantitative analysis). An instrument which measures an absorption spectrum is called a spectrometer.

Gaseous molecules are found only in discrete states of vibration and rotation, called the rovibrational state. Each such state, identified by quantum numbers describing both the vibration and rotation, has a single energy which depends on the quantum numbers. In dipole transitions described above, a single photon of radiation is absorbed, transforming the molecule from one ro-vibrational state to another. As the energies of the ro-vibrational states are discrete, so too are the energies of the transitions between them. Therefore, a photon must possess a specific energy to be absorbed by a molecule to transform the molecule between two given ro-vibrational states. Since the energy of a photon is proportional to the frequency of the radiation, (or equivalently, inversely proportional to its wavelength), only discrete frequencies (wavelengths) can be absorbed by the molecule. The set of discrete frequencies (wavelengths), often called absorption lines, at which a particular species of molecule absorbs, is called the absorption spectrum of a molecule. The width in frequency (wavelength) of each absorption line depends on the specific ro-vibrational transition, the pressure and temperature of the gas containing the molecule, and the presence (or absence) of other types of molecules in the gas. Each species of molecule has a unique absorption spectrum, by which the species of molecule may be identified. Since the energies of different rotational states of a gaseous molecule are typically spaced much more closely than the energies of different vibrational states, then the absorption lines occur in sets, each set corresponding to a single vibrational transition, and many rotational transitions. These sets of absorption lines are called absorption bands.

In the NIR, all the vibrational transitions are harmonics of fundamental, mid-infrared bands. These harmonics can be a hundred to ten thousand times weaker than their mid-infrared counterparts. Standard methods, such as Fourier Transform Infrared Spectroscopy (FTIR), commonly used to characterize mid-infrared transitions, normally have difficulty detecting these weak absorption features in the NIR spectral region. Therefore, more sensitive detection methods are required to measure NIR absorption features. Moreover, because overtone bands and combinations of overtone bands often overlap in wavelength (frequency), the NIR is normally filled with dense bands of absorption lines. It is therefore not uncommon to find spectral regions where the same molecular species has both strong and weak transitions that are co-located in wavelength (frequency). Hence, spectral resolution is very important, especially for near-infrared detection systems.

Measuring the concentration of an absorbing species in a sample is accomplished by applying the empirical Beer-Lambert Law. The Beer-Lambert law (or Beer's law) is the linear relationship between absorbance and concentration of an absorbing species. The general Beer-Lambert law is usually written as:

$$A(\lambda) = \alpha(\lambda)L = C\epsilon(\lambda)L \quad (1)$$

where $A(\lambda)$ is the measured absorbance, $\alpha(\lambda)$ is a wavelength-dependent absorption coefficient, $\epsilon(\lambda)$ is a wavelength-dependent extinction coefficient, L is the path length, and C is the analyte concentration.

Experimental measurements are usually made in terms of transmittance (T), which is defined as:

$$T = I/I_0$$

where I is the light intensity after it passes through the sample and $I_o$ is the initial light intensity. The relation between A and T is:

$$A = -\log T = -\log(I/I_o) \quad (2)$$

However, modern absorption instruments usually display the data as transmittance, %-transmittance, or absorbance, as a function of wavelength (or wave number). An unknown concentration of an analyte can be determined by measuring the amount of light that a sample absorbs, and then applying Beer's law. Equations (1) and (2) show that the ability of a spectrometer to detect a specific concentration depends not only on the path length through the sample, but also on the intensity noise of both the light source and the detector. Sensitivity can be quantified as a minimum detectable absorption loss (MDAL), i.e., the normalized standard deviation of the smallest detectable change in absorption. MDAL normally has units of $cm^{-1}$. Sensitivity can also be defined as the achievable MDAL in a one second measurement interval, and has units of $cm^{-1} Hz^{-1/2}$. Sensitivity accounts for the different measurement speeds achieved by diverse absorption-based methods and is a figure of merit for any absorption-based spectroscopic technique.

Typically, a spectral feature (called an "absorption peak") of the target species is measured in order to obtain its concentration. Although most species will absorb light at more than one wavelength, the total spectral profile of any particular species is unique. The ability of a spectrometer to distinguish between two different species absorbing at similar wavelengths is called selectivity. Because spectral features narrow as the sample pressure is reduced, selectivity can be improved by reducing the operating pressure. However, the spectrometer must still be able to resolve the resulting spectral lines. Thus, selectivity ultimately depends on spectral resolution. Spectral resolution, typically measured in frequency (MHz), wavelength (picometers) or wave numbers ($cm^{-1}$), is an important figure of merit for a spectrometer Optical detection is the determination of the presence and/or concentration of one or more target species within a sample by illuminating the sample with optical radiation and measuring optical absorption by the sample and a wide variety of optical detection methods are known. Most of these methods, however, have limited resolution, and can frequently not achieve sufficient selectivity in spectral measurement. For example, FTIR spectrometers can provide a very broad spectral tuning range but only at the expense of spectral resolution. Many FTIR spectrometers cannot resolve individual rotational lines in an absorption band at low operating pressures (below ~100 Torr). Non-dispersive infrared (NDIR) instruments have even less resolution that FTIR (typical filters cannot resolve individual rotational lines, let alone absorption bands) but enable inexpensive instruments. Tunable diode laser based absorption spectrometers (TDLAS), can achieve excellent wavelength resolution by finely tuning the laser. However, their precision and accuracy depend on being able to measure, and hence control, the laser wavelength. A TDLAS spectrometer is only as good as its wavelength measuring component. Cavity enhanced optical detection entails the use of a passive optical resonator, also referred to as a cavity, to improve the performance of an optical detector. Cavity enhanced absorption spectroscopy (CEAS) and cavity ring down spectroscopy (CRDS) are two of the most widely used cavity enhanced optical detection techniques. Cavity enhanced methods, like TDLAS depend in resolution on the quality of the wavelength monitoring device and resulting laser control. Both methods, however, provide a significant improvement in sensitivity over traditional TDLAS.

The intensity of single-mode radiation trapped within a passive optical resonator, called the ring-down cavity (RDC), decays exponentially over time, with a time constant $\tau$, which is often referred to as the ring-down time. In practice, it is desirable to ensure that only a single resonator mode has an appreciable amplitude, since excitation of multiple resonator modes leads to multi-exponential radiation intensity decay (i.e., multiple time constants), which significantly complicates the interpretation of measurement results. The ring-down time $\tau$ depends on the cavity round trip length and on the total round-trip optical loss within the cavity, including, of course, loss due to absorption and/or scattering by one or more target species within a sample positioned inside the cavity. Thus, measurement of the ring-down time of an optical resonator containing a target species provides spectroscopic information on the target species. Both CRDS and CEAS are based on a measurement of $\tau$.

In CRDS, an optical source is usually coupled to the resonator in a mode-matched manner, so that the radiation trapped within the resonator is substantially in a single spatial mode. The coupling between the source and the resonator is then interrupted (e.g., by blocking the source radiation, or by altering the spectral overlap between the source radiation and the excited resonator mode). A detector typically is positioned to receive a portion of the radiation leaking from the resonator, which decays in time exponentially with time constant $\tau$. The time-dependent signal from this detector is processed to determine $\tau$ (e.g., by sampling the detector signal and applying a suitable curve-fitting method to a decaying portion of the sampled signal). Note that CRDS entails an absolute measurement of $\tau$. Both pulsed and continuous wave laser radiation can be used in CRDS with a variety of factors influencing the choice. The articles in the book "Cavity-Ringdown Spectroscopy" by K. W. Busch and M. A. Busch, ACS Symposium Series No. 720, 1999 ISBN 0-8412-3600-3, including the therein cited references, cover most currently reported aspects of CRDS technology.

Single spatial mode excitation of the resonator is also usually employed in CEAS, but CEAS differs from CRDS in that the wavelength of the source is swept (i.e., varied over time), so that the source wavelength coincides briefly with the resonant wavelengths of a succession of resonator modes. A detector is positioned to receive radiation leaking from the resonator, and the signal from the detector is integrated for a time comparable to the time it takes the source wavelength to scan across a sample resonator mode of interest. The resulting detector signal is proportional to $\tau$, so the variation of this signal with source wavelength provides spectral information on the sample. Unlike CRDS, the CEAS technique entails a relative measurement of $\tau$. The published Ph.D. dissertation "Cavity Enhanced Absorption Spectroscopy", R. Peeters, Katholieke Universiteit Nijmegen, The Netherlands, 2001, ISBN 90-9014628-8, provides further information on both CEAS and CRDS technology and applications CEAS is also discussed in a recent article entitled "Incoherent Broad-band Cavity-enhanced Absorption Spectroscopy by S. Fiedler, A. Hese and A, Ruth Chemical Physics Letters 371 (2003) 284-294.

In cavity enhanced optical detection, the measured ring-down time depends on the total round trip loss within the optical resonator. Absorption and/or scattering by target species within the cavity normally accounts for the major portion of the total round trip loss, while parasitic loss (e.g., mirror losses and reflections from intracavity interfaces) accounts for the remainder of the total round trip loss. The sensitivity of cavity enhanced optical detection improves as the parasitic loss is decreased, since the total round trip loss depends more sensitively on the target species concentration as the parasitic loss is decreased. Accordingly, both the use of mirrors with very low loss (i.e., a reflectivity greater than 99.99 percent), and the minimization of intracavity interface reflections are important for cavity enhanced optical detection. Although the present invention will be described primarily in the context of CRDS, it should be understood that the methodology is also applicable to CEAS. In other techniques, called integrated cavity output spectroscopy (ICOS) and off-axis ICOS, the cavity is aligned so as to create a set of densely spaced modes, and with these techniques the method of this invention cannot be used. The present invention relies on the RDC clearly defining a comb of equally spaced modes (having the same transverse mode number and separated by the free spectral range). Such a comb of frequencies does not exist for ICOS cavities.

DESCRIPTION OF THE DRAWINGS

FIG. 4a is a schematic showing 2 and 3 mirror cavity configurations, both of which are suitable for the practice of the present invention. FIG. 4b illustrates wavelength monitor signal as a monotonic function of the laser wavelength.

In FIG. 7a note the monotonic, but not necessarily linear transfer function of the wavelength monitor. The array data are organized into bins and an average value of the decay time constant and wavelength is obtained for each bin.

FIG. 11 shows the first spectral scan and the selection of a reference bin. FIG. 12 shows the frequency dependence for a series of five measurements. FIG. 13 shows a more detailed image of the spectrum FIG. 14 shows how the frequency of an excited cavity mode can be determined with an accuracy higher than the accuracy achievable by an individual wavelength monitor measurement.

FIGS. 15a and 15b illustrates the applicability of the present invention to a V (15a) or ring cavity (15b) CRDS system.

DESCRIPTION OF THE INVENTION

Figure 1:
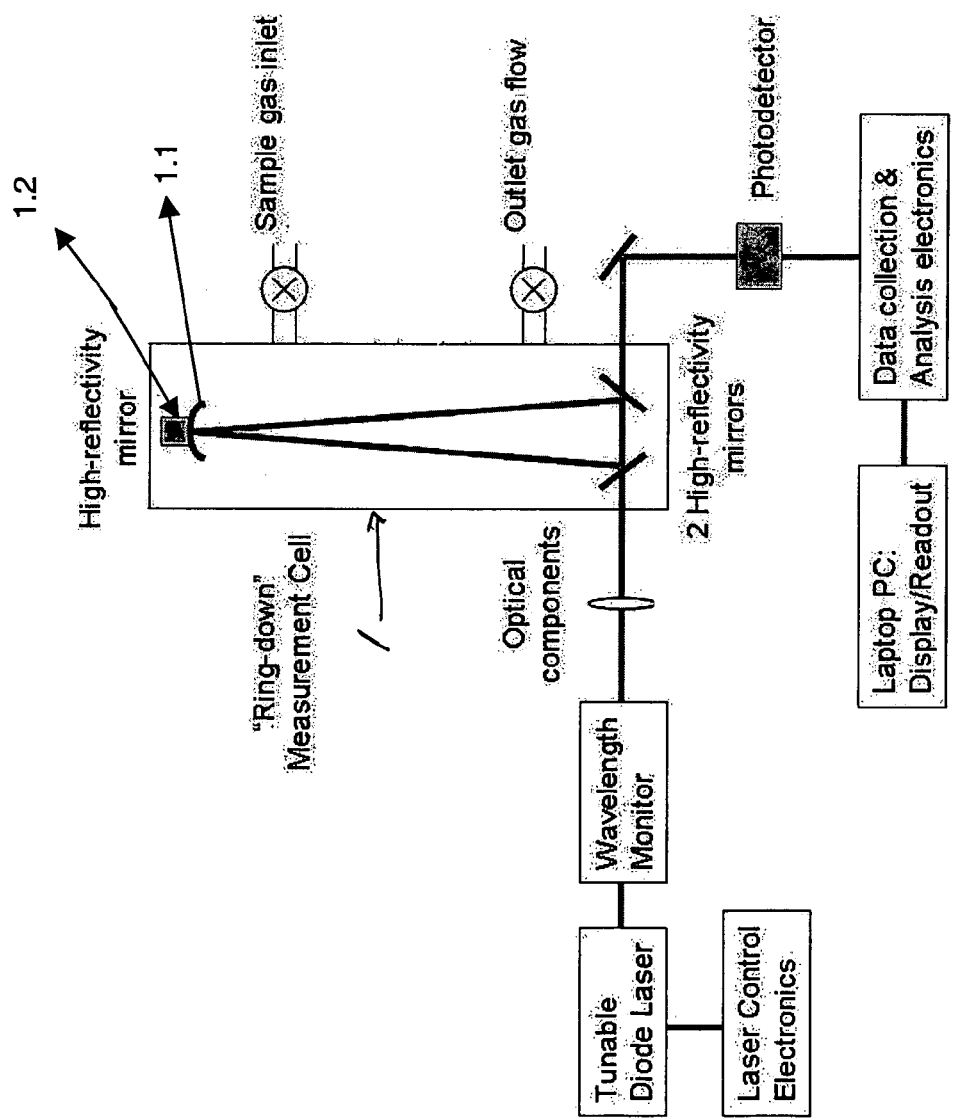
FIG. 1 illustrates a typical CRDS setup where one of the mirrors of the RDC is movable. This configuration uses the known "swept cavity" approach.

As previously indicated, none of the above-mentioned prior art absorption spectroscopy methods can measure the wavelength very precisely or accurately, and all of the laser-based methods, including CRDS and CEAS, have a spectral resolution that is only as good as the wavelength monitor used to measure and control the laser output. It is the purpose of the present invention to provide a wavelength measurement method that substantially increases the wavelength resolution of a CRDS or CEAS system, without requiring the use of a high precision wavelength monitor.

Furthermore, the method described herein does not require tight wavelength control of the laser source itself. Suitable lasers for the practice of the current invention include Distributed Bragg Reflector Lasers, Optical Parametric Oscillators, Optical Parametric Generators, External Cavity Diode Lasers and Distributed Feedback Lasers. All these lasers are of types known to the skilled artworker. Depending on the precise nature of the target analyte it may be possible to utilize a single laser which is tunable over a wavelength band suitable to cover all the absorption peaks of interest for the target analyte. For example, Distributed Feedback Lasers are tunable to emit radiation over a relatively broad wavelength range by varying the pump current to the laser and/or by altering the operating temperature of the laser. If an external cavity diode laser is utilized it will advantageously have a micromotor for wide range (coarse) tuning and a piezoelectric transducer (PET) for narrow range (fine) tuning. Another particularly suitable laser is an Optical Parametric Oscillator, which is another type of laser which provides a broad tuning range.

In a typical CRDS setup (FIG. 1), light from a laser is first injected into the RDC, and is then interrupted. The circulating light inside the RDC is both scattered and transmitted by the mirrors on every round-trip, and can be monitored using a photodetector placed behind one of the cavity mirrors. The decay constant, (ring-down time constant) $\tau$, is then measured as a function of laser wavelength to obtain a spectrum of the cavity optical losses. Detailed mathematical treatments of CRDS can be found in the previously cited book by Busch and Busch. A simple derivation is presented here.

For a given wavelength, $\lambda$, the transmitted light, $I(t,\lambda)$, from the RDC is given by $$I(t,\lambda)=I_0 e^{-t/\tau(\lambda)} \quad (3)$$

where $I_0$ is the transmitted light at the time the light source is shut off, and $\tau(\lambda)$ is the ring-down time constant. The total optical loss inside the cavity is $L(\lambda)=[c\tau(\lambda)]^{-1}$, where c is the speed of light. The total optical loss comprises the empty cavity optical loss plus the sample optical loss. As already indicated, CRDS provides an absolute measurement of these optical losses. The empty cavity (round-trip) optical loss, $L_{empty}(\lambda)$, comprises the scattering and transmission losses of the mirrors. In general, better mirrors provide both lower empty cavity losses and higher sensitivity. The sample (round-trip) optical loss is $A(\lambda)=\alpha(\lambda)l_{rt}$, where $l_{rt}$ is the cavity round-trip length, and is simply the difference between total cavity losses and empty cavity losses, namely, $A(\lambda)=L(\lambda)-L_{empty}(\lambda)$. Once the absorption spectrum, $\alpha(\lambda)$, of the sample has been measured, then the sample concentration can be readily computed using the absorption cross section and lineshape parameters.

The minimum detectable absorption loss (MDAL) for a CRDS system is defined by:

$$\alpha_{min} = \frac{1}{l_{eff}} \left( \frac{\Delta\tau}{\tau} \right), \quad (4)$$

where $\Delta\tau/\tau$ is called the shot-to-shot noise of the system. The effective path length of a CRDS measurement is $l_{eff}=l_{rt}/L_{empty}$. For typical RDC mirrors having a reflectivity of 99.995%, and thus scattering losses of less than 0.0005%, the path length enhancement can exceed 20,000. For a 20 cm long sample cell, the effective path length is 8 km, which surpasses the best performance of multi-pass spectroscopy by a factor of three, based on effective path length alone. A good CRDS system can achieve a shot to shot variation of 0.03 to 0.04%, leading to a MDAL of $3\times10^{-10}$ cm$^{-1}$. Note also that the CRDS measurement is not dependent on either the initial intensity of the light inside the cavity, provided that the signal has a sufficient signal to noise ratio at the detector, or on the physical sample path length, unlike traditional absorption spectroscopy.

Figure 2:
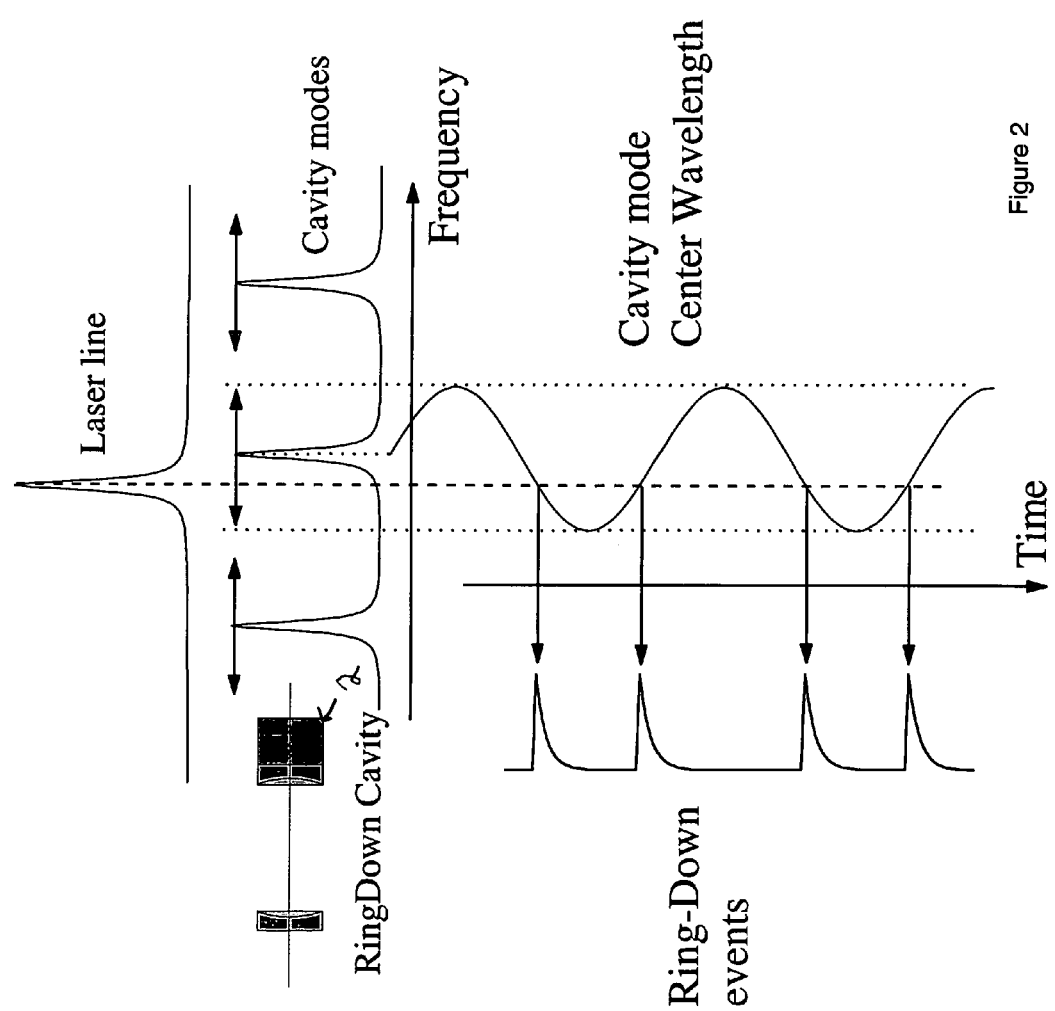
FIG. 2 illustrates the principle of operation for the swept-cavity implementation of CRDS. The laser line is swept around a mode of the optical resonator and produces a ring-down signal at every coupling event.

The most common CRDS implementation, often called a "swept-cavity" setup, uses a ringdown cavity (RDC) having one mirror (1.1) translatably mounted on a piezoelectric (PZT) or other transducer (1.2) as is shown in FIG. 1. The swept-cavity principle is illustrated in FIG. 2. One mirror (2.1) is translated so as to change the cavity length by half a wavelength. When sufficient light build-up inside the cavity is detected, the light source is either turned off, or an external modulator such as an acousto-optic modulator (AOM) deflects the light away from the RDC. For spectral tuning, the laser is set at specific wavelengths using the wavelength monitor, and the RDC length is changed so as to sweep at least one mode of the cavity through the laser. This is always true if the RDC length is modulated by one half of the operating wavelength. The RDC length can also be tracked using a tracking circuit, which adjusts the PZT offset to maximize the repetition rate of the ring-down events. The mirror is then moved only very little around the laser line. Each time that the laser is stepped in wavelength, the tracking circuit reacquires the PZT offset to maximize the repetition rate. Thus, the ring down events occur in bursts with high repetition rate, in between longer periods of time wherein the PZT offset is being determined.

The principal limitation of the swept-cavity approach is that its frequency resolution depends directly on the resolution and performance of the wavelength monitor employed. The system relies directly on knowing the exact wavelength monitor transfer curve (wavelength versus monitor output), on the calibration of this transfer curve, and on its stability over time due to device aging. Finally, the dependence of the system on a high quality wavelength monitor can increase its size and inevitably results in a higher price. In turn, a large size and a high price will limit the range of applications for which the instrument can be deployed.

The swept-cavity method also depends on the ability to set and maintain the laser wavelength with accurate and reproducible control. For this reason, swept-cavity approaches often exploit distributed feedback (DFB) diode lasers. DFB lasers are very controllable and can be operated with high reproducibility. However, when using DFB lasers, the swept-cavity approach often becomes slow, because the DFB laser must be locked to each wavelength in the spectral scan, which can take time (e.g., if the laser is thermally controlled). Moreover, if the laser is directly modulated (e.g., laser current is shut off), then the laser must recover to the appropriate wavelength before data acquisition can continue, which further slows down the data acquisition rate. If the external modulation is employed to solve this issue, unnecessary costs are introduced into the system. Moreover, the tuning range of DFB lasers is limited. Typical tuning ranges of available lasers are 30 GHz of continuous, high resolution (resolution better than 10 MHz) current tuning, with a total tuning range (range of current tuning increments) of 3 to 4 nm, based on temperature tuning. Although it is relatively straightforward to find absorption lines for either a single species or two isotopes of a species that fall within such a tuning range, the laser tuning range frequently limits the capability of the CRDS instrument to one, or at most several, species.

However, broadly and rapidly tunable laser sources are becoming available. External cavity diode lasers (ECDLs) offer tuning ranges of at least 40 nm, and 120 nm appears achievable. Optical parametric oscillators already provide even broader tuning ranges. These lasers, however, often do not provide good wavelength control or become very large and expensive when good wavelength control is implemented. Furthermore, for broadly tunable CRDS systems (>40 nm), high resolution and precision wavelength monitors having reproducible calibration, and which are small, inexpensive, robust and reliable, do not exist.

An alternative approach (FIG. 3) which has been proposed, is to dither the laser wavelength around a given cavity mode while keeping the cavity length constant. The dotted vertical lines shown as 3.1 denote the cavity mode spacing. The dithering is shown as 3.2. The dots 3.3 on solid line curve 3.4 indicate the average value of the frequency (wavelength). Dashed vertical lines 3.5 and 3.6 show the effect of a first and second change in the cavity length by a fraction of a wavelength. The laser is tuned from cavity mode to cavity mode in order to trace out the spectrum. Note that because the laser wavelength is being changed, this approach has less wavelength accuracy than the approach where the laser wavelength is set to a constant value. Moreover, if the cavity length is kept constant, the resolution of the system is limited to the free spectral range (FSR) of the cavity, which can be comparable to the spectral width of the absorption features being measured. For example, at 50 Torr pressure for a 20 cm long RDC having a FSR of 714 MHz, the absorption lines for many species will only have a spectral width of several GHz, so that only a handful of spectral points can be measured (as illustrated in FIG. 2).

Figure 3:
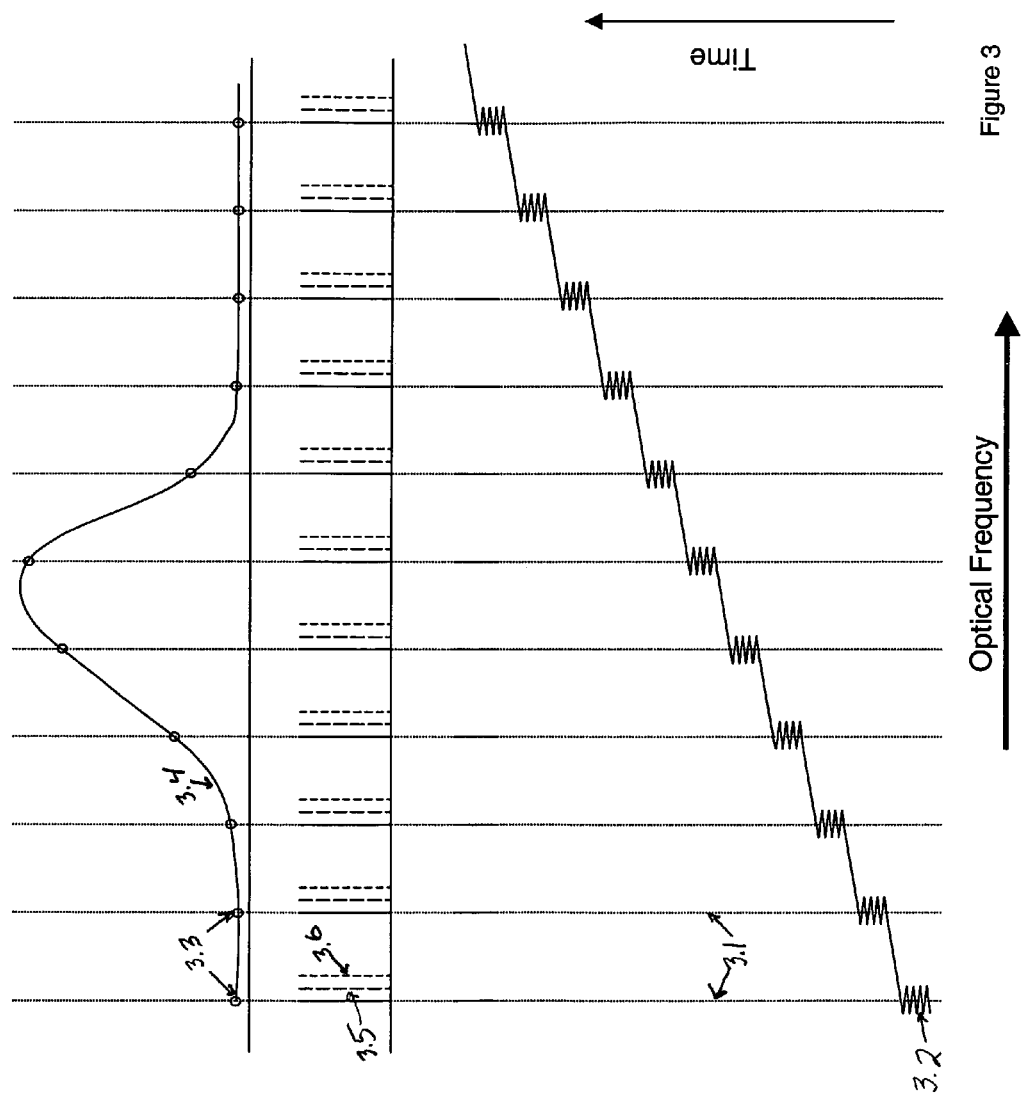
FIG. 3 illustrates how a sequence of the same longitudinal modes (for a fixed transverse mode) in an optical resonator creates an equidistant set of frequency references. The positions of all the cavity mirror are fixed, while the laser is swept around each mode of the optical resonator multiple times in order to collect ring-down events. The dotted lines represent the same array of cavity frequencies when the position of one of the cavity mirrors is altered using a transducer to thereby change the cavity length by a fraction of a wavelength.

In order to resolve the resolution limitation, Paldus and Harb (U.S. Pat. No. 6,377,350) proposed to use the cavity at a fixed length as a comb of equidistant frequencies. The laser is swept through this comb over the desired spectral range (or spectral features) and then the cavity length is changed, in order to generate the next frequency comb, which is slightly shifted in frequency from the first. A series of interleaved comb sequences (dotted lines in FIG. 3) is obtained, thereby improving the overall spectral resolution. Thus, the above-indicated patent by Paldus and Harb teaches the use of a ringdown cavity (RDC) to generate a series of well-referenced frequency combs, but it does not teach how to generate highly accurate wavelength measurements from this series of combs. The wavelength of each initial cavity mode wavelength in a comb must still be determined using a wavelength monitor, because the other wavelengths (frequencies) in this comb are only known relative to the first frequency. Although this approach improves the speed of taking data (only the first wavelength in each comb-must be wavelength controlled and measured accurately), it still relies on an accurate and high precision wavelength monitor. Furthermore, the patent assumes that if multiple ring-down events need to be averaged at each mode in a given comb sequence, that the laser can be dithered around that mode (FIG. 3). There is therefore an implicit assumption that the laser wavelength can be changed in a controllable and repeatable manner. The aforementioned Paldus and Harb patent fails to teach how to tune the laser when it is not easily controllable, and achieve the same benefits of the equidistant frequency comb of cavity modes. Unfortunately, many broadly tunable lasers, such as external cavity diode lasers, OPOs, or DBR lasers have poor frequency control and reproducibility.

Figure 4:
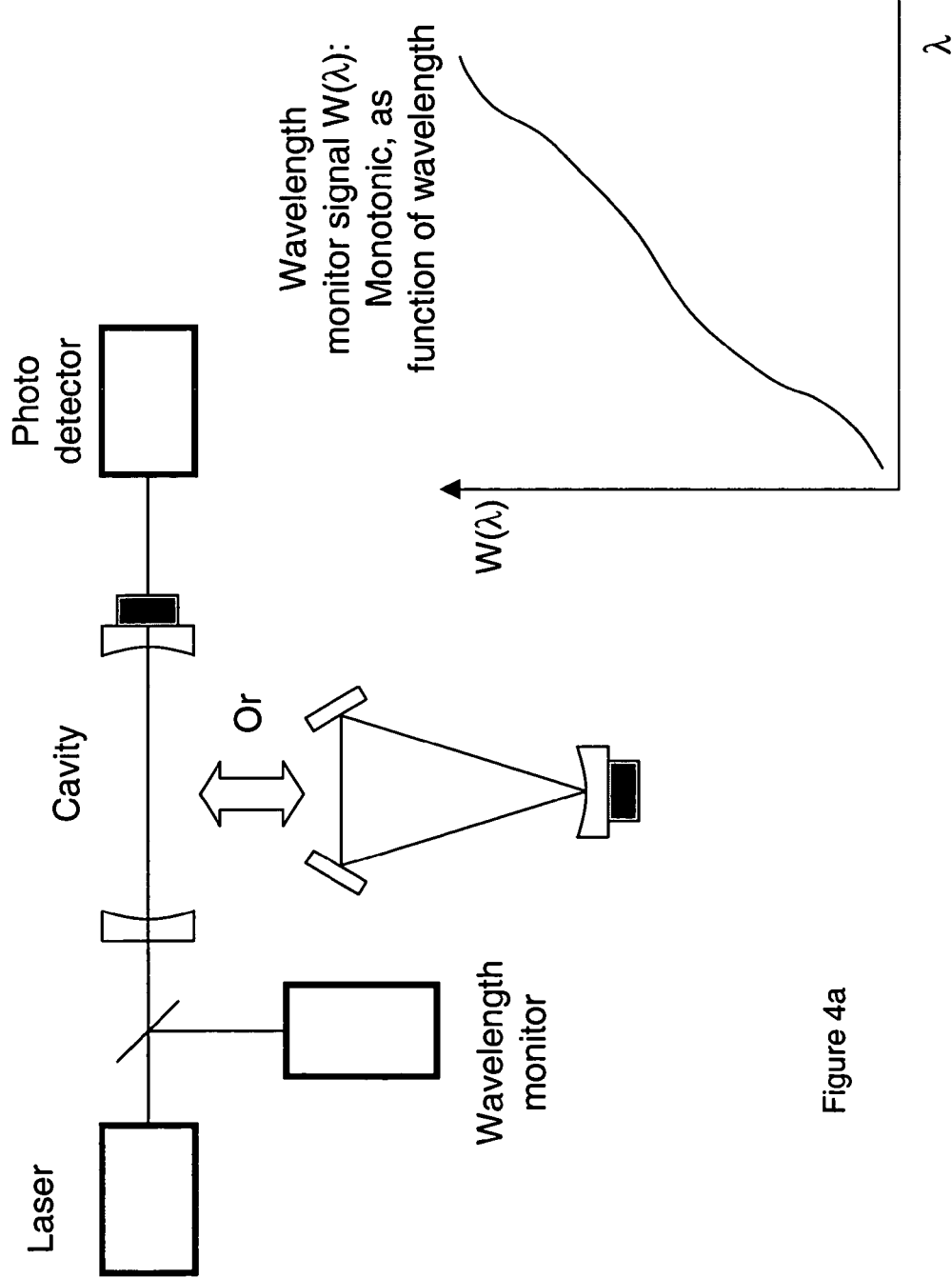
FIGS. 4a and 4b shows two alternative embodiments of the current invention. The system of the present invention requires only a coarse, inexpensive wavelength monitor having resolution comparable to the cavity free spectral range (FSR).
Figure 5:
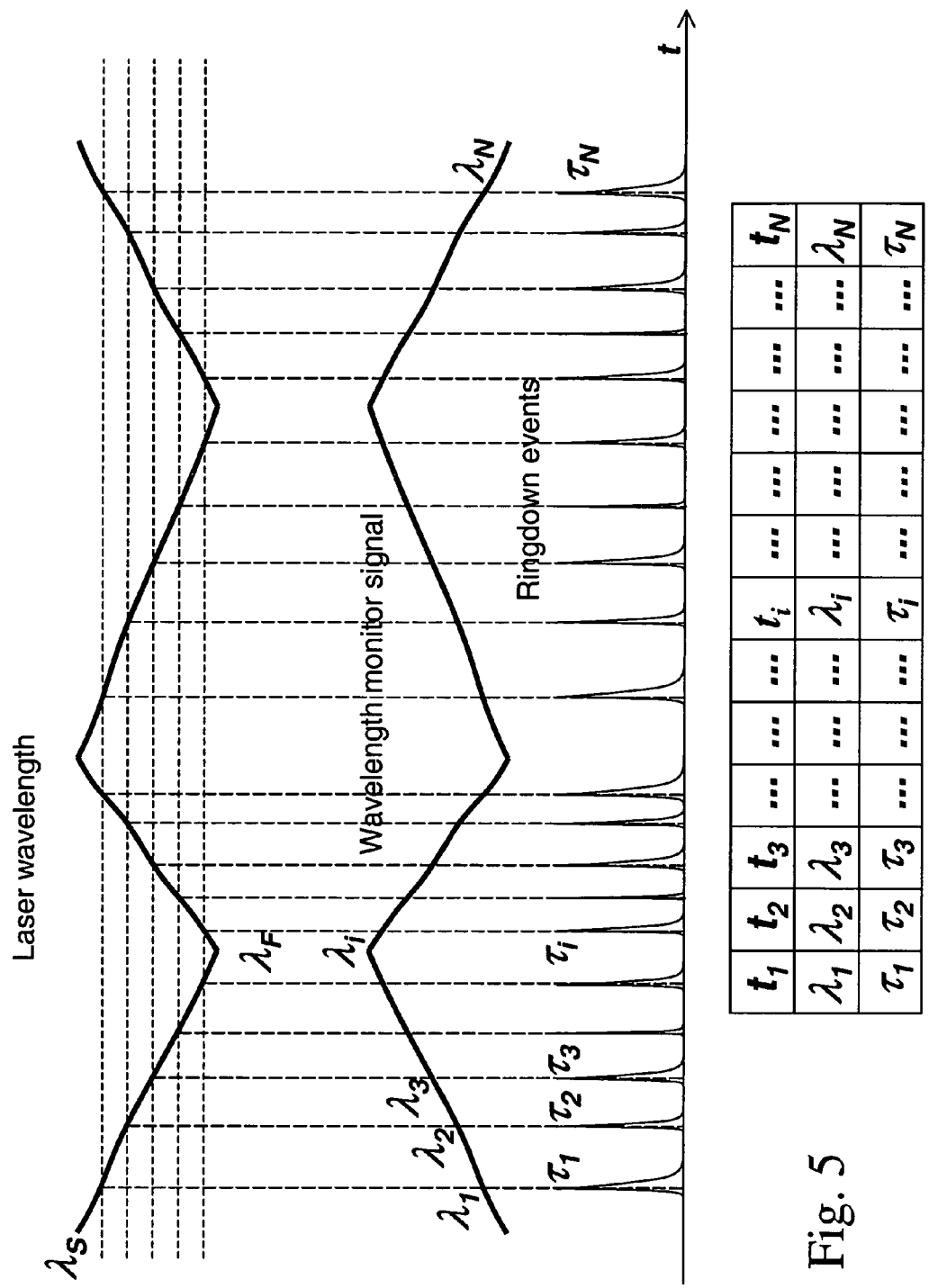
FIG. 5 illustrates the timing diagram of the frequency binning system of the present invention. The laser is tuned over multiple cavity free spectral ranges from start wavelength $\lambda_1$ to end wavelength $\lambda_2$. For every ring-down event, the trigger time ($t_i$), the wavelength before shut-off ($\lambda_i$) and the ring-down time constant ($\tau_i$) are recorded. The laser is swept multiple times over the selected spectral range.

It is the purpose of our invention to resolve the limitations inherent in the Paldus/Harb patent, so that a CRDS or CEAS using an inexpensive wavelength monitor and a relatively poorly controllable laser can be used. The only requirement on the wavelength monitor transfer function is that it be monotonic. Note that it can be either increasing or decreasing, preferably increasing. The setup for the approach of the present invention is shown in FIG. 4. The laser can either be directly or externally modulated to obtain the ring-down events. FIG. 5 shows the timing diagram of the frequency binning data acquisition process. The laser is tuned over multiple cavity free spectral ranges from start wavelength $\lambda_s$ to an end wavelength $\lambda_e$. For every ring-down event, the following three parameters ($t_i$, $\lambda_i$ and $\tau_i$) are recorded and an index i is assigned for each parameter:

1. the trigger time ($t_i$): measured as the time at which the laser is shut off
2. the wavelength before shut-off ($\lambda_i$): measured by taking multiple wavelength measurements prior to each triggering event, and averaging the last N wavelengths taken.
3. the ring-down decay time constant ($\tau_i$): measured by detecting the ring-down exponentially decaying waveform and fitting it for the decay time constant The laser is swept multiple times over the selected spectral range for a fixed cavity length. An array of trigger time, wavelength and ring-down time constant is constructed, and organized as a function of trigger time. Note that the temporal spacing of the ring-down events can be very uneven, so that the data rate is aperiodic. An average data rate can then be determined over multiple sweeps of the wavelength range. The decay times in the array are in no particular order by cavity mode. The cavity modes are characterized by the coarse wavelength measurement however.

Figure 6:
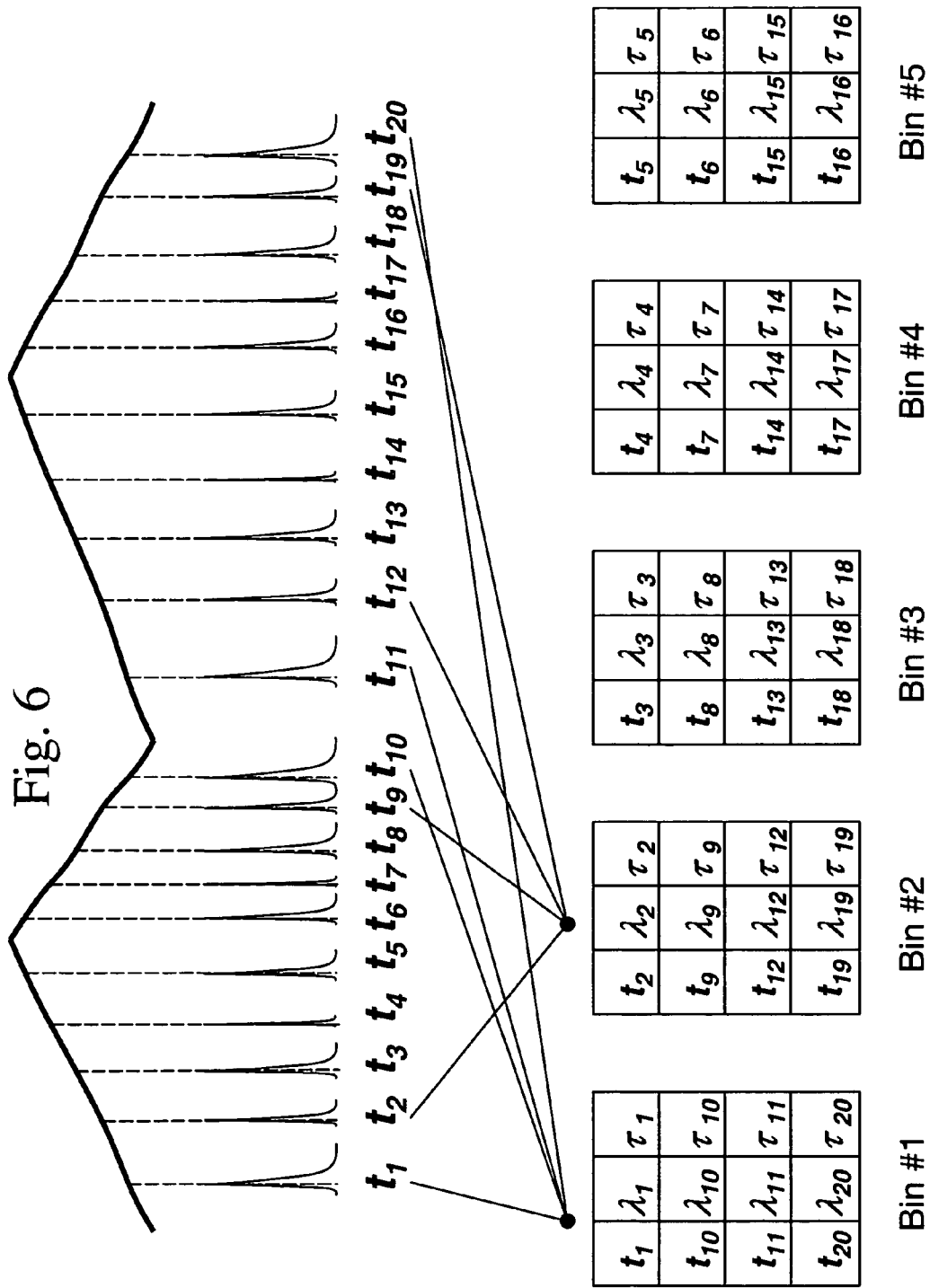
FIG. 6 illustrates the reorganization of the data array into "bins". The sorting is done by coarse wavelength. The coarse wavelengths correspond to RDC modes.
Figure 7B:
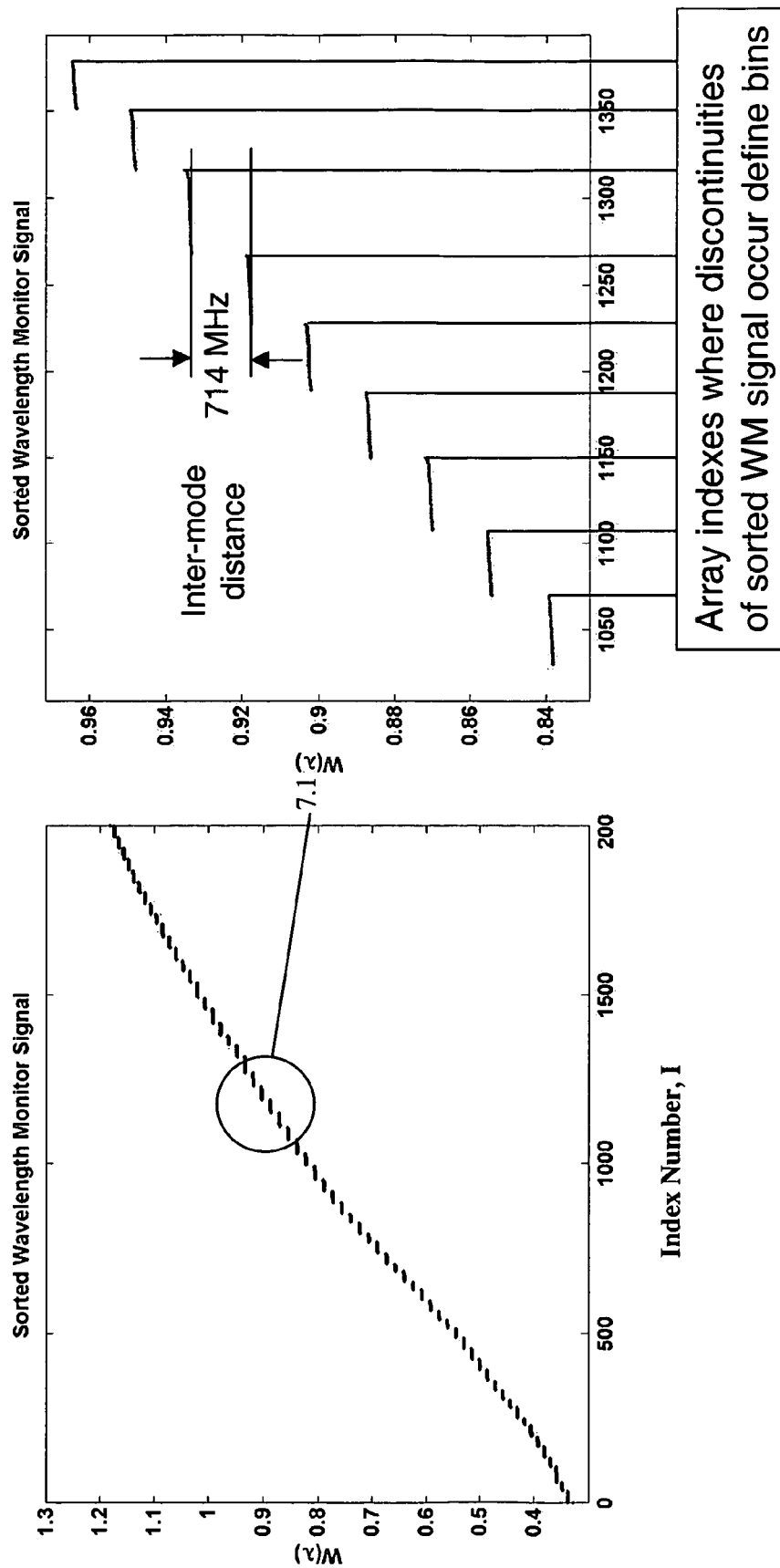
FIGS. 7a and 7b illustrate, respectively, spectral data organized by wavelength monitor signal (or wavelength) over a specified tuning range, as a function of bin number, and detail from a plot of monitor signal as a function of bin number, clearly illustrating the "staircase" of bin wavelengths.
Figure 7A:
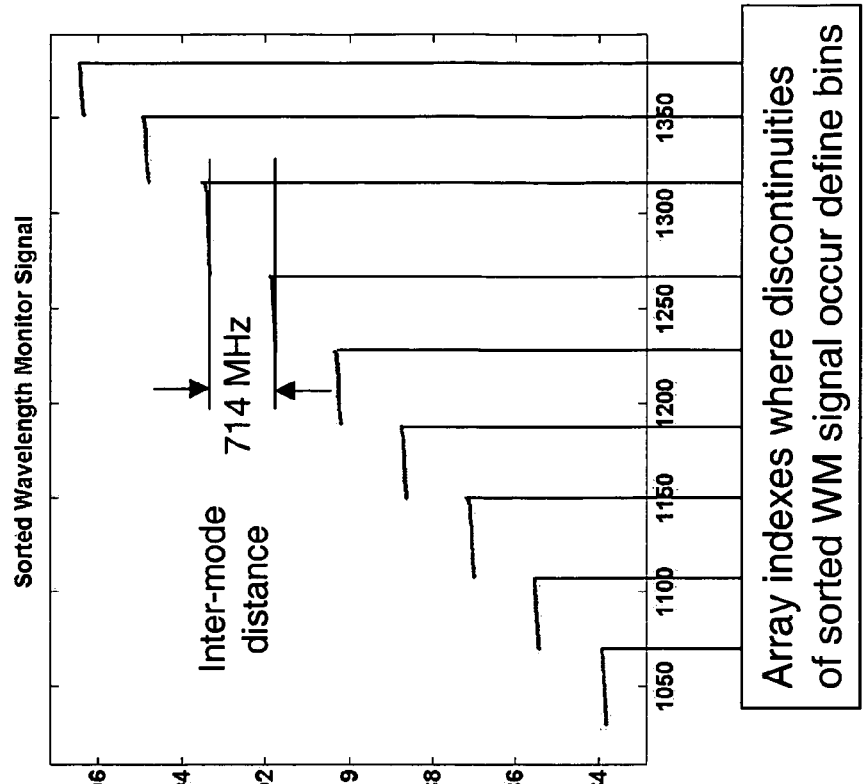

These data are then processed as illustrated in FIG. 6:
1. the wavelengths are ordered (sorted) by increasing value and assigned a new index I. The discontinuities of the sorted wavelength monitor signal define the boundaries between groupings of wavelengths having a similar value, called "bins" each of which has a bin index j,
2. The ordered wavelengths can be plotted on a chart showing wavelength as a function of ordered array index I (FIG. 7a). The data forms a staircase where each step is separated in frequency by the free spectral range of the cavity. Each step is assigned a bin number, and corresponds to a RDC cavity mode (7b). The bins are defined by discontinuities occuring in the sorted wavelength modulation signal. The steps are not flat, but have error bands that correspond to the precision of the wavelength monitor. The average wavelength in each bin group is computed as $\lambda_j$ and assigned a bin index, j. Note that in order to be able to accurately bin the decay constants by cavity mode, the resolution of the wavelength monitor need only be better than one third the spectral range of the RDC.
3. Once the wavelength binning is established, the index I of the ordered wavelength is used as an index to re-group the trigger time and decay time constants into parallel bins.
4. Within each such bin, the decay time constants are arranged by increasing trigger time. Note that different bins can contain different numbers of decay constants.
5. The average decay time for each bin, $\tau_{j,ave}$, is computed and $\tau_{j,ave}$ is then converted into optical absorption loss, $\alpha_{j,ave}$.

Figure 8:
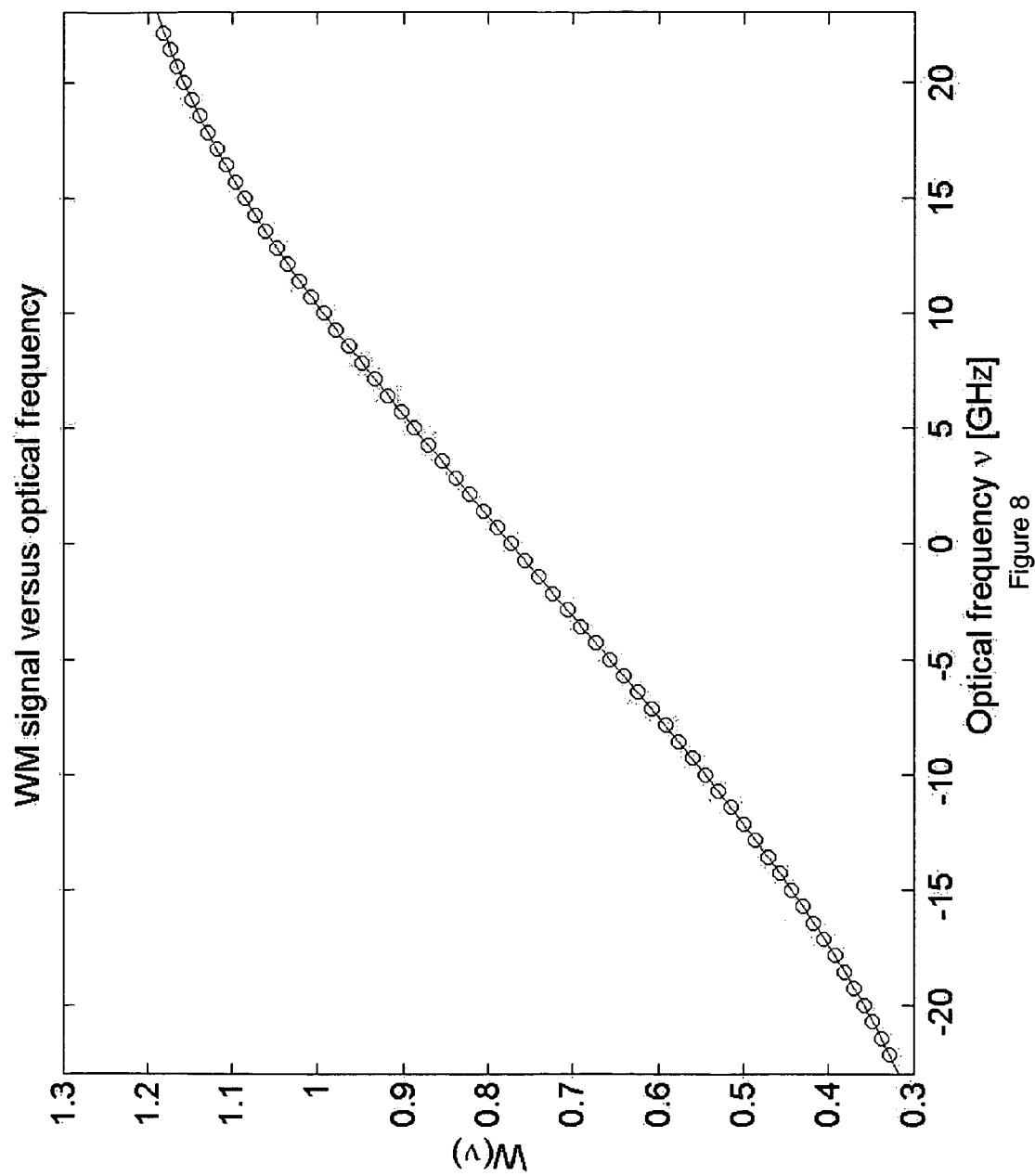
FIG. 8 shows the wavelength monitor function that is obtained by interpolating the measured wavelengths using a spacing equal to the free spectral range(FSR) of the ring-down cavity (RDC).

The wavelength monitor function can then be obtained by fitting the array of averaged wavelengths, $\lambda_{j,ave}$, with the spacing set to the free spectral range of the RDC (FIG. 8). Note that this approach does not require an a priori knowledge of the wavelength monitor transfer function, and in fact, generates this transfer function. Thus, by periodically fitting the wavelength data, the system can compensate for any aging or other induced changes in the wavelength monitor transfer function. The only criterion required is that the transfer function be monotonic.

There are several known prior art methods and devices, generally referred to as wavelength monitors or wavemeters, that produce outputs proportional to the frequency (wavelength) of the laser light input to the monitor. Wavelength monitors utilize one or more optical filters, such as transmission filters, reflection filters, interferences filters, Fabry-Perot etalons, etc., and associated photo-detectors to provide the wavelength readout. Some examples of wavelength monitors, suitable for use in the present invention, that use one or more optical filters to provide wavelength readout include U.S. Pat. Nos. 4,815,081; 6,122,301; 6,400,737; 6,289,028 and 4,172,663, the teaching of which are incorporated herein by this reference.

In one embodiment, the wavelength monitor is an etalon, preferably a wedge etalon, with two photodetectors. The optical signal is incident on the etalon at a pre-determined angle to obtain the interference pattern between light reflected off or from the front surface and the back surface of the etalon. The monotonic (linear) portion of the etalon is used to provide the wavelength-dependent response. The etalon will preferably be thin in order to maximize the linear range of operation.

Preferably, the optical filter has a wavelength-dependent response that is linear. In one preferred embodiment, the wavelength monitor is a transmission filter with two photodetectors. More specifically, the actual filter is a coating on a piece of glass. In another embodiment, the wavelength monitor is a reflection filter, also with two photodetectors, where the filter is a coating on a piece of glass. In another embodiment the wavelength monitor can be a photodetector having a coating whose wavelength response is linear. All these types of optical filters are inexpensive and small, and will normally have sufficient wavelength resolution for the frequency-sequencing application of the present invention.

Figure 9B:
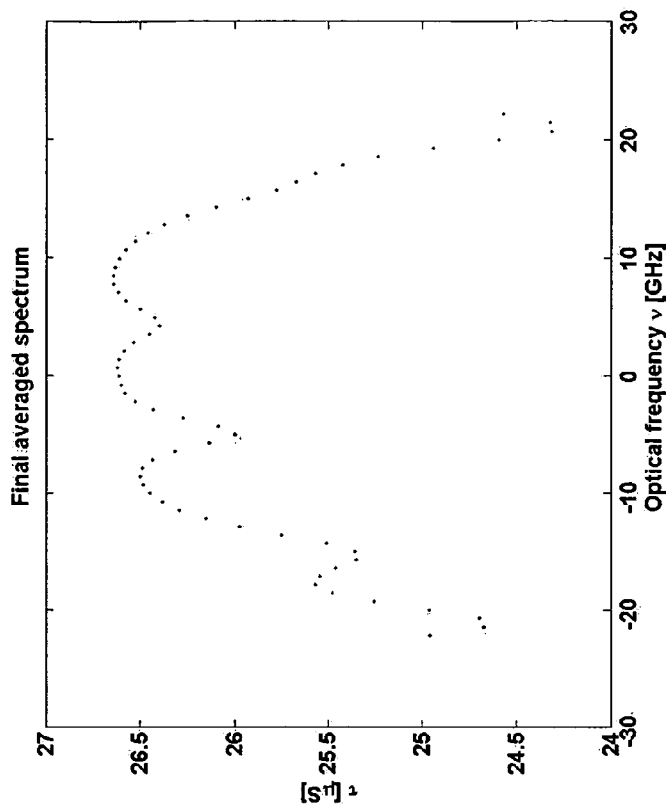
FIGS. 9a and 9b show the measured spectrum using (9a) raw data for wavelength and ring-down time constant, and (9b) averaged data for ring-down time constant and computed data from the fitted wavelength monitor transfer function for the wavelength.
Figure 9A:
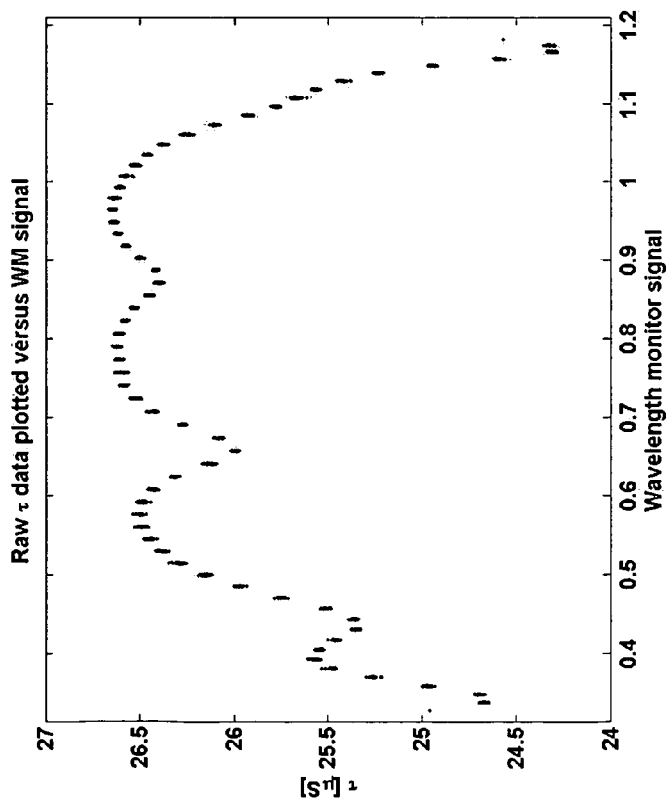

The measured spectrum is then obtained by plotting the optical loss, $\alpha_{j,ave}$, versus the average wavelength, $\lambda_{j,ave}$. FIGS. 9a and 9b compare the spectrum obtained by plotting the raw data 9a (re-ordered decay time as a function of reordered wavelength monitor signal) and the averaged data 9b ($\alpha_{j,ave}$ versus $\lambda_{j,ave}$). Note that averaging reduces both the error in the measured optical loss value, as well as the measured wavelength. An additional benefit of the frequency binning approach is that the inherent noise in the laser frequency is reduced by using the cavity modes as a reference. The laser frequency noise appears in the trigger time as a noise contributor, but does not affect the final measured spectrum. This is not the case in traditional swept-cavity approaches, where the laser noise can significantly affect the spectral measurement. Wavelength monitor noise and uncertainty are reduced in this approach by averaging of the wavelength measurements, but most importantly by generating a fitted function using the RDC free spectral range (FSR) as a reference. Thus, the measured wavelengths obtained are highly accurate, even for very broad tuning ranges. Moreover, the frequency-binning approach of the present invention is self-referencing by using the RDC FSR.

In order to compare system performance in sensitivity between swept-cavity CRDS and frequency-binned CRDS, the shot to shot noise is compared. For typical swept-cavity systems, shot-to-shot fluctuations do not exceed 0.1%, while for good swept-cavity systems, they are the order of 0.03-0.04%. FIG. 9a presents data obtained from the same hardware used as a swept-cavity system, but operated as a frequency-binned system. The swept-cavity system shot-to-shot noise was 0.04%. Clearly, for the frequency binning method, the shot to shot fluctuations remain approximately the same, and hence substantially identical sensitivities can be expected from frequency-binned systems as for swept-cavity systems having the same optical hardware design.

Figure 10:
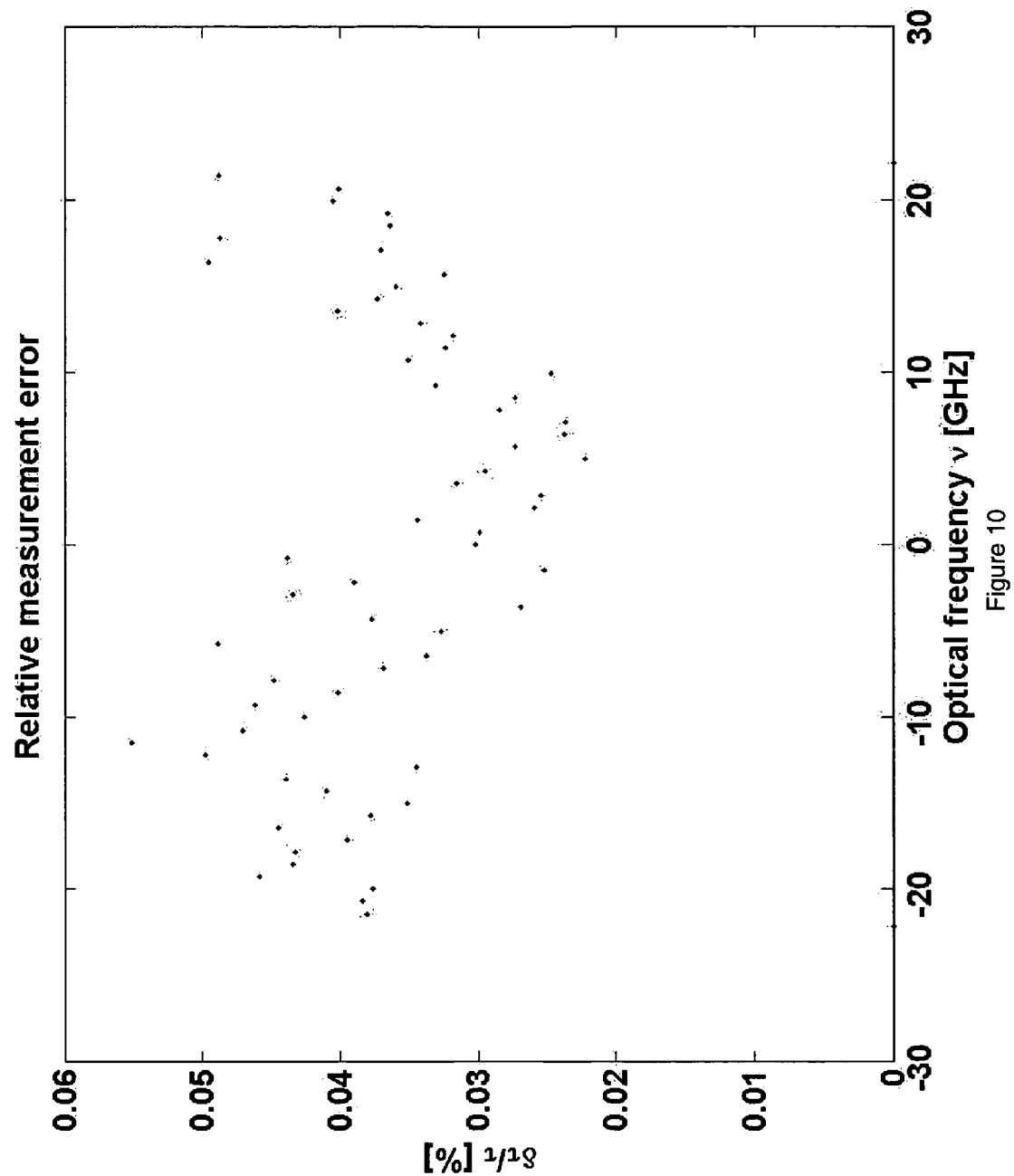
FIG. 10 shows the shot-to-shot noise as a function of wavelength "bin" over a spectral range when the frequency-binning method is applied.

There is no sensitivity penalty resulting from using the frequency-binning approach. On the contrary, there is a substantial benefit in performance resulting from binning. Frequency binned systems have more precise wavelengths. In the traditional swept-cavity method the wavelength of the recorded ringdown event is determined by the instantaneous wavelength of the laser for the event. There always exists some laser wavelength jitter, and therefore the ringdowns that belong to the same wavelength data point will each be registered at a slightly different frequency. This jitter makes no difference in the ringdown time at the flat portions of the spectrum (the baseline), but wavelength jitter will result in larger ringdown time variations along the slope of the absorption line. For this reason, the performance of swept-cavity CRDS is usually characterized at the baseline, not at the slope. With the binning approach of the present invention, the cavity length is fixed and the ringdown time variation at any fixed mode frequency is determined only by the system performance. This is clearly visible in FIG. 9a. The spread of the recorded ringdown times is the same on both the slopes of the absorption lines and on the baseline. Such observation is further confirmed in FIG. 10, where the ringdown time measurement error corresponding to the spectrum shown in FIG. 9a is plotted as a function of the optical frequency. Across the entire spectrum scan the error is approximately 0.04%, and it does not increase on the absorption line slopes.

We should stress that the final averaged spectrum obtained with the binning approach, such as shown in FIG. 9b, is plotted versus optical frequency using known cavity mode spacing. The wavelength monitor data are not used, and therefore, the wavelength accuracy, and more importantly, the linearity of the wavelength (or optical frequency) scale does not depend on the wavelength monitor performance. The cavity mode frequency separation can be very accurately determined by measuring a spectrum with known absorption lines positions, and they thus become a frequency standard for any particular CRDS apparatus. Absorption lines such as those of acetylene ($C_2H_2$) are used as frequency references in telecom systems.

Usually in CRDS the temperature of the cavity should be maintained at a constant temperature for the simple reason that the absorption lines intensities are strongly temperature dependent. Usually, the cavity temperature is stabilized within ±0.001 K. The cavity body is preferably made of Invar, which has a thermal expansion coefficient of about $10^{-6}$. The cavity will then change its length only by one part in $10^9$, resulting in excellent linearity and accuracy of the frequency axis obtained with the binning approach.

Even though the cavity is maintained at constant temperature, its mode frequencies may still drift slowly due to other factors. For example, when the sample gas is passed through the cavity (when taking the spectrum in continuous flow mode as opposed to a batch mode), small pressure variations may cause small changes of the cavity mode frequencies. Or, if one of the cavity mirrors is mounted on a piezo-electric transducer (PZT), the position of such mirror can drift, especially immediately after the voltage applied to the PZT is changed.

Figure 11:
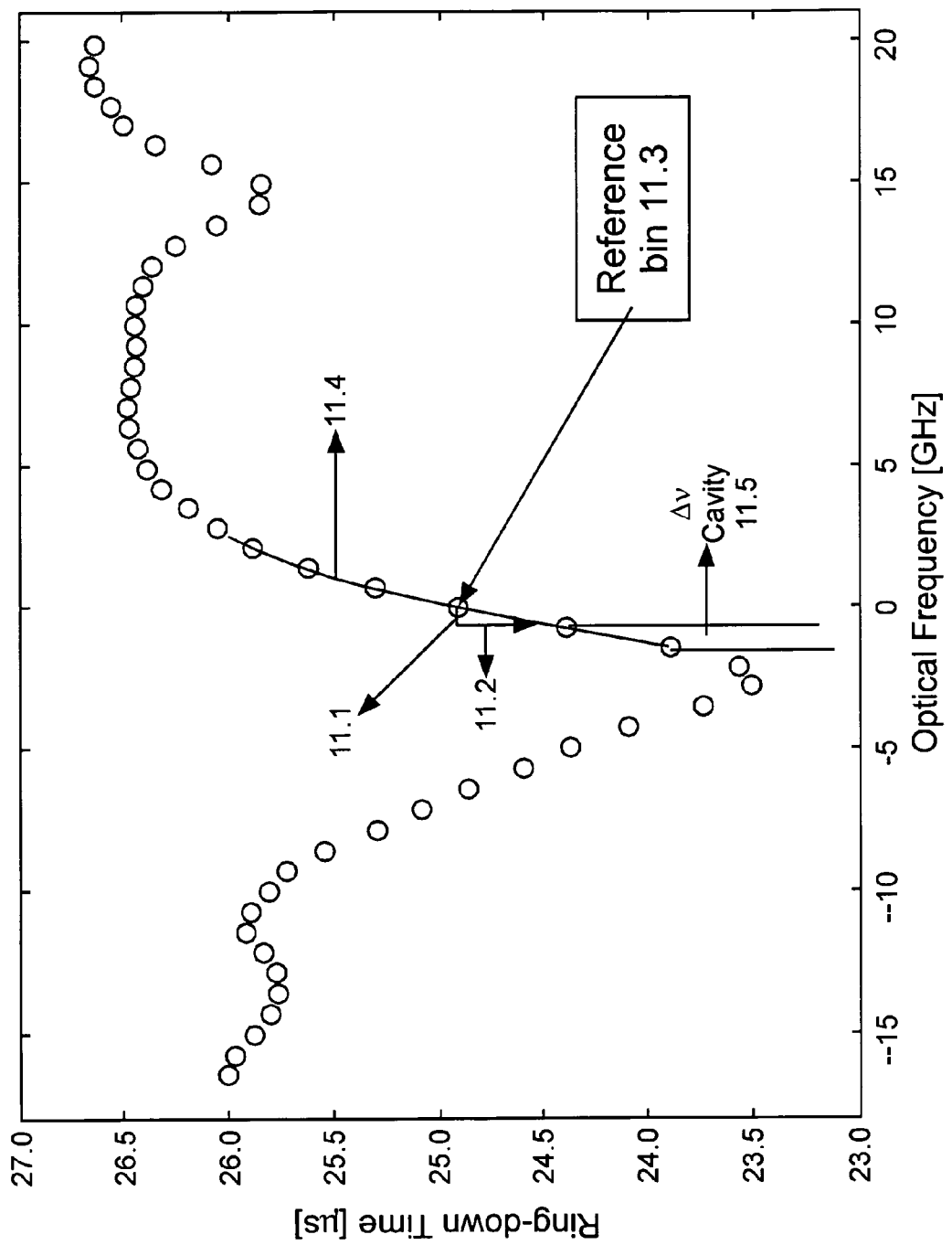
FIGS. 11 through 13. illustrate the capability of the binning technique to accommodate cavity length change (and hence mode position drift during the measurement period.

The frequency binning technique has an additional benefit in that it can accommodate such cavity length changes (and hence mode position drift) during the measurement period. Consider a series of several binned spectra. The first measurement (spectrum) of the series is shown in FIG. 11. If the mode frequency positions shift between the first and second spectra, as shown by short horizontal line 11.1, then the absorption seen by this mode will change as shown by vertical arrow 11.2. Therefore, the change of the absorption for a particular bin (e.g., "reference bin" 11.3) is a measure of the mode frequency drift. It is advantageous to choose such a reference bin on the slope of a strong absorption line in the spectrum. Such strong absorption lines belonging to the background gases generally exist in high-sensitivity spectroscopy in the vicinity of the absorption lines of the species of interest (target analyte). Usually they are found to be a problem, but using our approach they can be used for calibration. The conversion from absorption to frequency drift of the reference bin can be done by taking several bins on either or both sides of the reference bin, and fitting their positions with a smooth curve, to a lower order polynomial, for example, as is shown by solid line 11.4 in FIG. 11. The frequency separation of exactly one inter-mode distance between the bins gives the exact frequency scale, shown as 11.5 ($\Delta v$ cavity).

Figure 12:
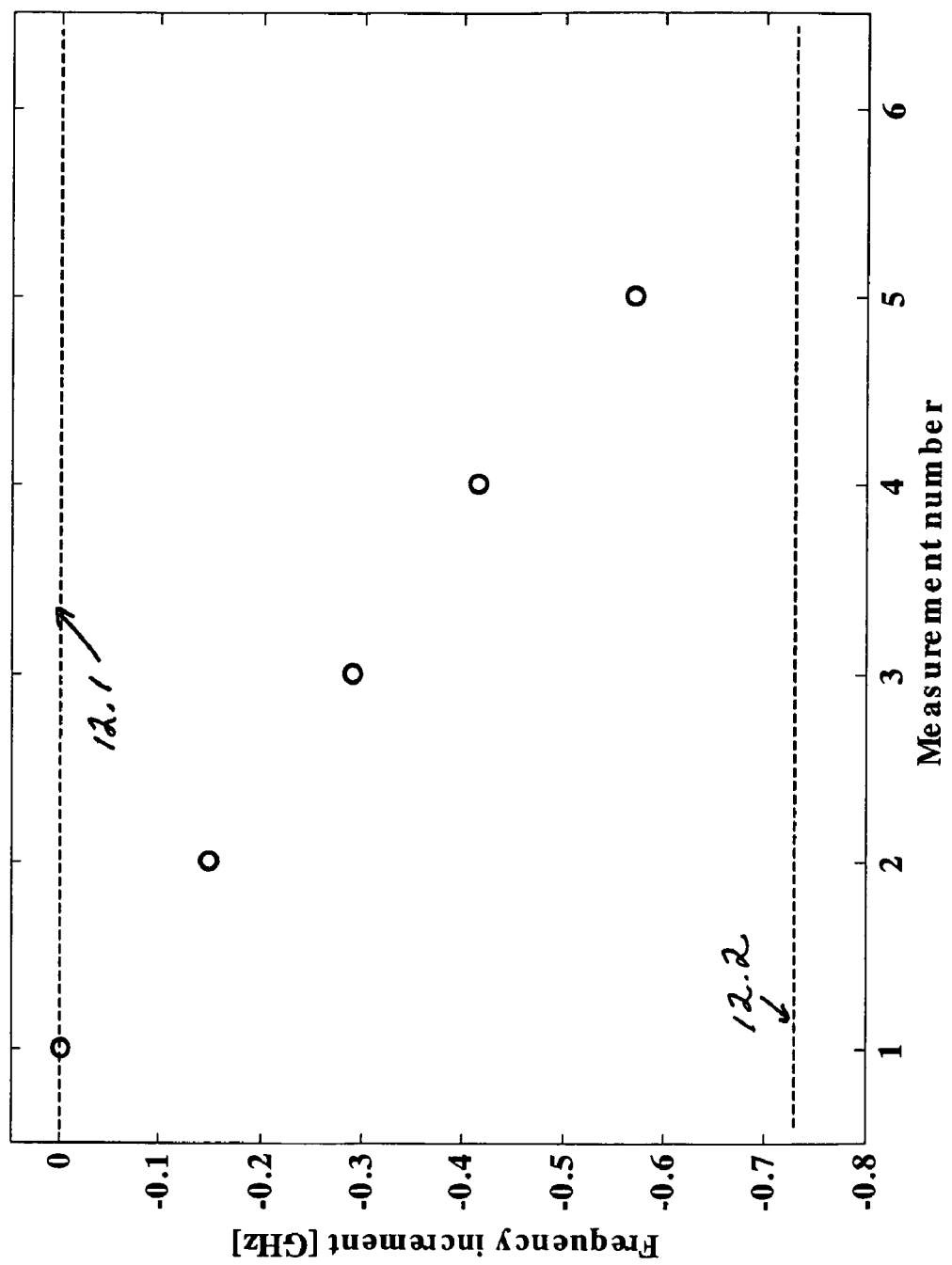
Figure 13:
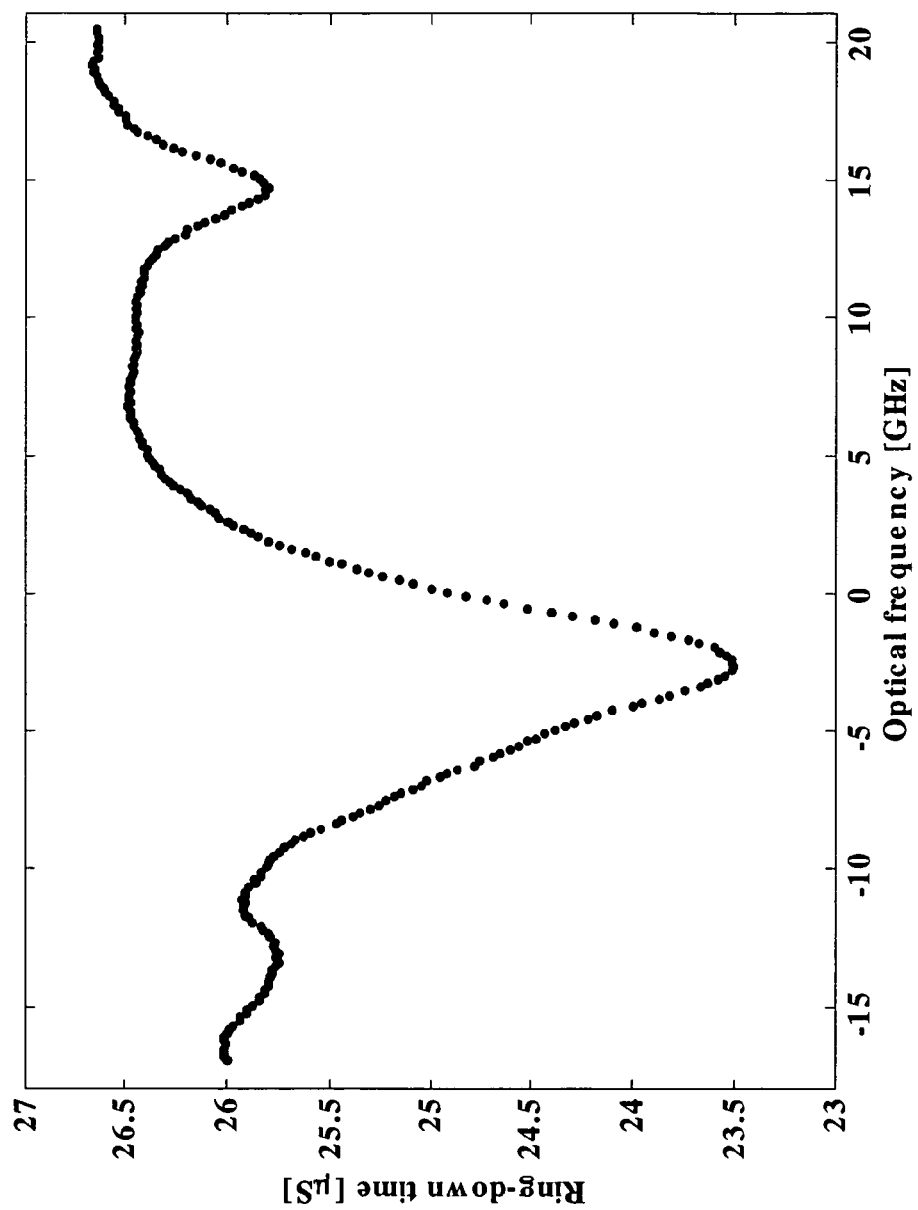

Once the function that converts the absorption change for the reference bin into optical frequency deviation for this reference bin has been determined from a first measurement, the function can now be applied to calculate the exact frequency position for all measurements in the series. An example of such a frequency dependence for a series of five measurements is shown in FIG. 12. The cavity mode positions for the first measurement are shown in this Figure by the two horizontal dotted lines 12.1 and 12.2. Knowing the positions of the interleaved frequency mode combs for each of five interleaved measurements we can plot an interleaved spectrum (FIG. 13), which gives us higher resolution. The spectral resolution of the interleaved spectrum is five times better than the mode spacing of the cavity.

In the previous paragraph we have described how the absorption changes on the slope of an absorption line in the spectrum can be used for determining the exact frequencies of the mode comb even in presence of cavity optical length changes. Additionally, it will be evident to a skilled artworker, that such cavity length changes can be intentionally applied via the PZT, for example, in order to obtained a frequency-corrected, interleaved spectrum with a spectral resolution much higher than the cavity mode spacing. All that is needed is to record N spectra, and apply between each of the recordings a cavity length increment resulting in the mode comb shift of 1/N of the free spectral range.

Another benefit of frequency binning is that it can accommodate cavity length change (and hence mode position drift) during the measurement period. For a given bin (or cavity mode), the optical loss (or decay time) is plotted as a function of trigger time. If the optical loss changes, it is an indication that the cavity length was drifting. A calibration for each bin can be made by fitting the changes in absorption to the spectral absorption feature at the wavelength corresponding to the bin number. Any cavity length drift can then be compensated for by applying the temporal drift function to the raw wavelength data.

A final benefit of the frequency-binning approach is that it can accommodate wavelength monitor drift during the measurement period. After the cavity length drift correction is made to the wavelength data, the measured wavelength can be plotted as a function of trigger time for each bin (or cavity mode). The frequency drift of the wavelength monitor can then be extrapolated and a correction applied to the wavelength data.

The final spectrum can be obtained by plotting the corrected wavelength data against the optical loss. At each step, the resolution of the wavelength monitor is improved: when the wavelengths are averaged by the number of measurements in a bin, when the wavelength monitor transfer function is computed, and finally when both cavity length drift and wavelength monitor drift corrections are applied.

As in the previous case, once a full array at a fixed cavity length has been analyzed, the RDC length can be adjusted by an intermode distance, and the entire measurement/analysis sequence repeated. The final resolution of the measurement will depend on the number of intermode sequences used. The number of intermode sequences required is determined by the resolution specified and the RDC FSR. For example, a 20 cm RDC cavity has a FSR of 714 MHz, so that in order to obtain a resolution of 10 MHz, 70 intermode sequences must be used.

Once all of the intermode sequences are obtained and analyzed, they can all be interleaved to obtain the final spectrum. The final spectrum should have sufficient resolution to define the spectral features and be able to perform an accurate fit of the absorption line shape. Note that up to this point, the actual wavelength measurements are all relative and that the intermode spacing is also not completely defined. The peak positions are then fit to the data of the combined sequence, so that absolute wavelengths of one bin in each sequence are obtained. These establish the absolute wavelength of each sequence, and therefore of the overall spectrum. The calibrations and extrapolations can then be extended to broader wavelength regions.

Another embodiment of the frequency-binning method can be particularly advantageously applied specifically to a DFB laser. DFB lasers can be turned off within a fraction of a microsecond by simply shutting off their drive current, or by shorting their anode and cathode down by means of an electronic switch. This eliminates the need for an acousto-optic modulator (AOM) and thus simplifies the CRDS system and reduces its cost. As is usual in CRDS, the laser is preferably kept off until the whole ring-down signal has been digitized, and then the laser can be turned on for the next ring-down to occur. However, a DFB laser (and more generally, any kind of a semiconductor laser) has the property of the frequency "chirping" in the range of a few GHz on startup. In conventional swept-cavity CRDS, the laser defines the optical frequency at which the absorption is sampled, and therefore the DFB laser must be first locked to the desired optical frequency, before the detection of the ring-down events be carried out. Such locking can be done with a feedback loop that adjusts the DFB laser temperature and current using the wavelength monitor signal as a reference. This approach has certain disadvantages. First of all, such locking requires time, and this reduces the sampling rate of the spectrometer. The second disadvantage is that the noise in the wavelength monitor electronics sets a limit on the frequency precision. With the binning approach of the present invention, there is no need to lock the DFB laser, as the optical frequency is defined by the cavity mode frequency grid. Additionally, the frequency of the specific cavity mode that is optically excited can be determined with an accuracy that exceeds the accuracy of an individual wavelength monitor measurement, as illustrated in FIG. 14.

Figure 14:
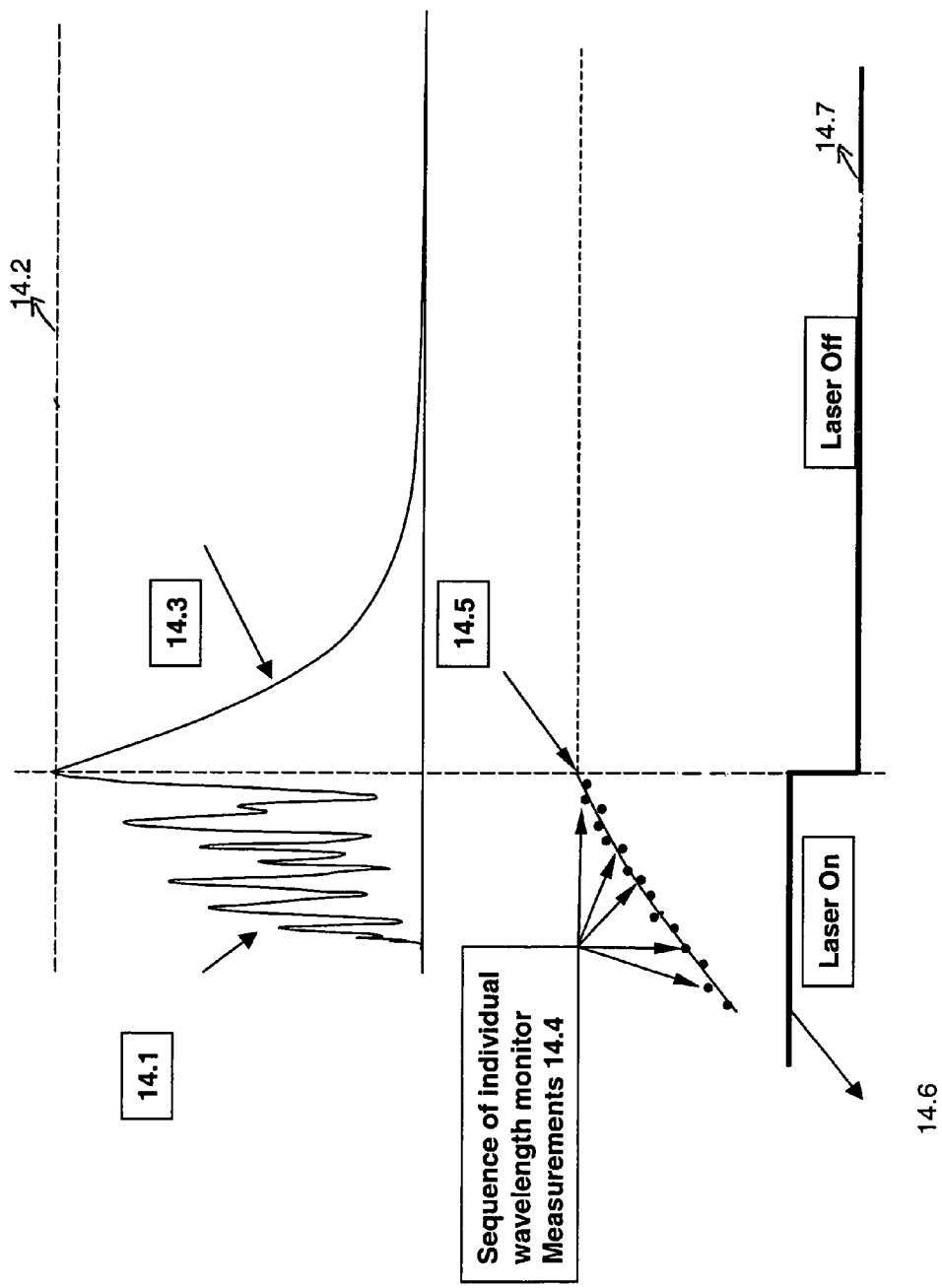

The top trace in FIG. 14 (14.1) shows the initial intensity buildup inside the cavity when the chirping DFB mode approaches the cavity mode position. The buildup trace noise is caused by the DFB laser phase noise. When the buildup intensity reaches a predefined ringdown threshold value (shown in FIG. 14 by a horizontal dashed line 14.2), the trigger circuit sends the cut-off signal to the laser current, resulting in a smooth ring-down waveform (14.3) being observed. The middle trace in FIG. 14 shows the DFB laser wavelength in the approach to the trigger event. The wavelength monitor signal is being measured at a repetition rate defined by the bandwidth of the wavelength monitor electronics, and the results of individual measurements are shown in by dots. These results are stored in the data processor memory (pre-trigger mode) and fitted by a low-order polynomial (least squares fit). The values of this polynomial are shown in the middle trace of FIG. 14 by solid line (14.5). This solid line has improved the accuracy of the wavelength determination by the square root of the number of processed pre-trigger points. The more precise value for the cavity mode frequency can be determined as the value of this polynomial at the trigger point. Assuming 100 pre-trigger point measured for each ring-down, a 10-fold improvement can be achieved. In addition, as now there is no need to lock the laser frequency, much higher ring-down acquisition rates become possible. The bottom trace shows the laser on (14.6) and off (14.7) sequence in conjunction with the traces shown in 14.1 through 14.5.

Even though the principle of measuring several wavelength monitor signal values before the trigger to improve the accuracy of the wavelength determination has already been described in the context of a DFB laser, it will be clear to a person skilled in the laser art that the same principle can be applied to additional classes of lasers. By way of example we describe two alternative lasers. However, we would like to stress that the class of useable lasers is not limited to these two described types. The first laser is a Fabry-Perot (F-P) diode laser. These lasers can have single frequency operation, and their frequency can be tuned by current or temperature. The difference between a F-P and a DFB laser is that a F-P laser mode hops (i.e., it does not tune continuously in wavelength). When the Fabry-Perot diode is switched on and off repeatedly, it can alternate between one or another of the longitudinal modes of its Fabry-Perot cavity. Such a property makes tuning a Fabry-Perot laser very complex, (there is no frequency selection mechanism as in a DFB laser) and this will render them generally unsuitable for a traditional swept-cavity CRDS. The mode hopping is not a problem for the frequency binning method of the present invention, once we determine the wavelength of the laser for each ring-down.

A second example of a suitable laser is a Fabry-Perot chip with an antireflection coating on one of its facets and an external cavity arrangement. A spectral filter can be installed in the external cavity in order to force such F-P external cavity laser to operate at a desired wavelength within the gain bandwidth of the chip. Such an external cavity laser has a short separation of its external cavity longitudinal mode frequencies and therefore an even higher probability of mode hopping. Typically, the longitudinal mode separation can be of the order of 5 to 10 GHz. Our described binning approach will still permit one to determine the optical frequency to which every ring-down event should be attributed, independent of the mode hops. If the laser average current and temperature are kept constant, the ringdowns will cluster around the external cavity mode frequencies of the laser, separated by 5 to 10 GHz. However, all that is needed in order to record the entire spectrum is to change the average current or temperature (or both) during the spectrum acquisition so as to fill up the gaps between the modes. It should be noted that such a laser has traditionally been deemed unsuitable for swept cavity CRDS.

Finally, it should be noted that cavity-swept optical configuration for CRDS or CEAS that use linear or ring cavities are not the only possible CRDS embodiments to benefit from the frequency-binning approach of the present invention. An optical feedback V-cavity CRDS system, as illustrated in FIG. 15a, or on optical feedback a ring-cavity CRDS system, as shown in FIG. 15b, can also be combined with the frequency binning approach of the present invention. One benefit of the V-cavity approach is that the injection efficiency into the RDC is significantly increased, thereby improving the signal-to-noise ratio on the ring-down photodetector, and potentially resulting in improved shot-to-shot noise. Another benefit is that the optical locking between the laser and the cavity (such as for a ring cavity) can increase the effective repetition rate of the data acquisition. The laser can, for example, be a DFB laser or a conventional or external cavity Fabry-Perot laser.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

The invention claimed is:

1. A process for measuring the absorption spectrum of a target analyte using a cavity ring down spectrometer comprising a tunable laser light source, a wavelength monitor which measures the wavelength of the light emitted by said laser and provides an output signal based on said measurement, and a resonant optical cavity, said process comprising the steps of:
   i) tuning said laser such that the light transmitted from said laser into said cavity is varied over a wavelength interval $\lambda_s$ to $\lambda_E$, said interval being chosen to encompass both the absorption wavelength of a spectral feature of said target analyte and a plurality of the free spectral ranges of said optical cavity;
   ii) shutting off the transmission of light into said cavity to thereby trigger a ringdown event;
   iii) repeating steps i) and ii) a plurality of times;
   iv) for each said ringdown event, recording the decay time constant $\tau$, the wavelength of the light transmitted into the cavity immediately prior to shutting off transmission, and the trigger time at which the light is shut off;
   v) organizing the decay time constants, light wavelength and trigger times recorded in step (iv) as a function of trigger time;
   vi) ordering said light wavelengths by increasing value and placing groups of wavelengths into individual bins, said groups being defined by discontinuities in the wavelength monitor signal;
   vii) computing the average wavelength of each bin group;
   viii) grouping the decay time constants and trigger times into bins that parallel said wavelength bins, with the decay time constants in each of said parallel bin being arranged by increasing trigger time;
   ix) computing the average decay time for each decay time bin identified in step (viii) and using this decay time average, together with the average wavelength from the parallel wavelength bin, to compute the optical loss for the target analyte at said average wavelength;
   x) providing said computed optical loss as an output.

2. A process in accordance with claim 1 wherein said laser is a Distributed Feedback Laser, a Fabry-Perot Laser, a Distributed Bragg Reflector Laser, an External Cavity Diode Laser or an Optical Parametric Oscillator Laser.

3. A process in accordance with claim 1 wherein said wavelength monitor signal increases monotonically with increasing wavelength.

4. A process in accordance with claim 1 wherein said wavelength monitor signal is a transmitted or reflected signal from a Fabry-Perot etalon.

5. A process in accordance with claim 1 wherein said wavelength monitor signal is a transmitted or reflected signal from a linear filter.

6. A process in accordance with claim 1 wherein said wavelength monitor is a photodetector having a linear coating.

7. A process in accordance with claim 1 wherein said resonant optical cavity is a linear, ring or V-cavity.

8. A process in accordance with claim 1 wherein said resonant optical cavity is maintained at a substantially constant temperature.

9. A process in accordance with claim 1 comprising the additional step of compensating for any changes in the length of said resonant optical cavity during the course of said measurement process.

* * * * *